US00PP21006P3

(12) United States Plant Patent
Toftness

(10) Patent No.: US PP21,006 P3
(45) Date of Patent: May 25, 2010

(54) CHERRY TREE NAMED 'TIP TOP'
(50) Latin Name: *Prunus avium*
Varietal Denomination: Tip Top

(75) Inventor: Troy M. Toftness, Wenatchee, WA (US)

(73) Assignee: Tip Top Orchards LLC, Wenatchee, WA (US)

( * ) Notice: Subject to any disclaimer, the term of this patent is extended or adjusted under 35 U.S.C. 154(b) by 0 days.

(21) Appl. No.: 12/284,634

(22) Filed: Sep. 23, 2008

(65) Prior Publication Data

US 2010/0077520 P1 Mar. 25, 2010

(51) Int. Cl.
*A01H 5/00* (2006.01)

(52) U.S. Cl. ..... Plt./181

(58) Field of Classification Search ..... Plt./181
See application file for complete search history.

*Primary Examiner*—June Hwu
(74) *Attorney, Agent, or Firm*—Michelle Bos

(57) ABSTRACT

'Tip Top' is a new and distinct cherry tree notable for its sweet, crisp fruit, reduced tendency to bruise, non-browning flesh, and early maturity as compared to 'Rainier'.

5 Drawing Sheets

Genus and species: *Prunus avium.*
Variety denomination: 'Tip Top'.

BACKGROUND AND SUMMARY OF THE VARIETY

The new cherry variety 'Tip Top' originated as a chance seedling of unknown parentage. The seedling was found in a commercial 'Sweetheart' cherry (not patented) orchard planted in 2001 near Wenatchee, Wash. In 2005, it was observed that the seedling was markedly different from the surrounding trees. It was similar in appearance to a 'Rainier' cherry tree (not patented), but was distinguished from 'Rainier' by its sweeter, more crisp fruit and its early maturity. Additionally, fruit of the newly discovered plant was found to be resistant to bruising and browning. Trees were propagated from the seedling by budding onto 'Mazzard' rootstock near Wenatchee, Wash., to determine whether the desired characteristics of the chance seedling would carry through to asexually propagated progeny. It has been found that the distinguishing characteristics of the tree and fruit of the newly discovered variety are reproduced through asexual propagation and have remained stable through successive generations.

'Tip Top' is a new and distinct cherry tree notable for its sweet, crisp fruit, reduced tendency to bruise, non-browning flesh, and early maturity as compared to 'Rainier'.

BRIEF DESCRIPTION OF THE PHOTOGRAPHS

Figure 1:
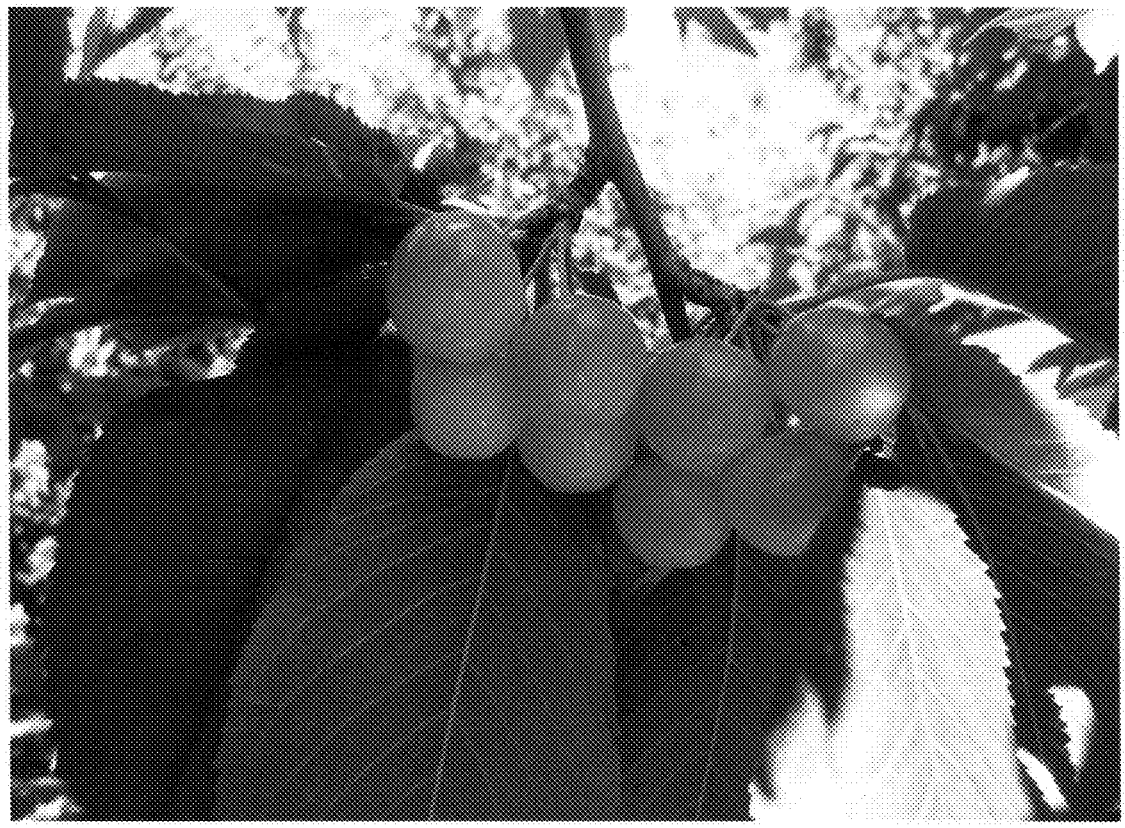
Figure 2:
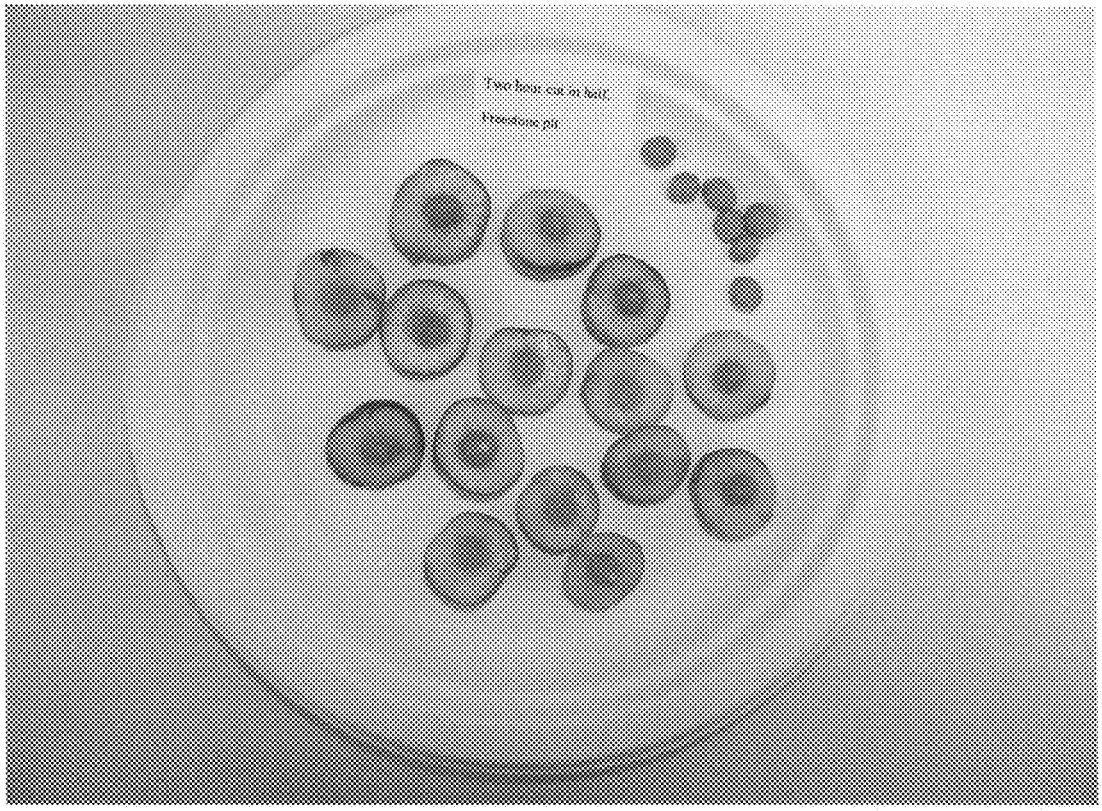
Figure 3:
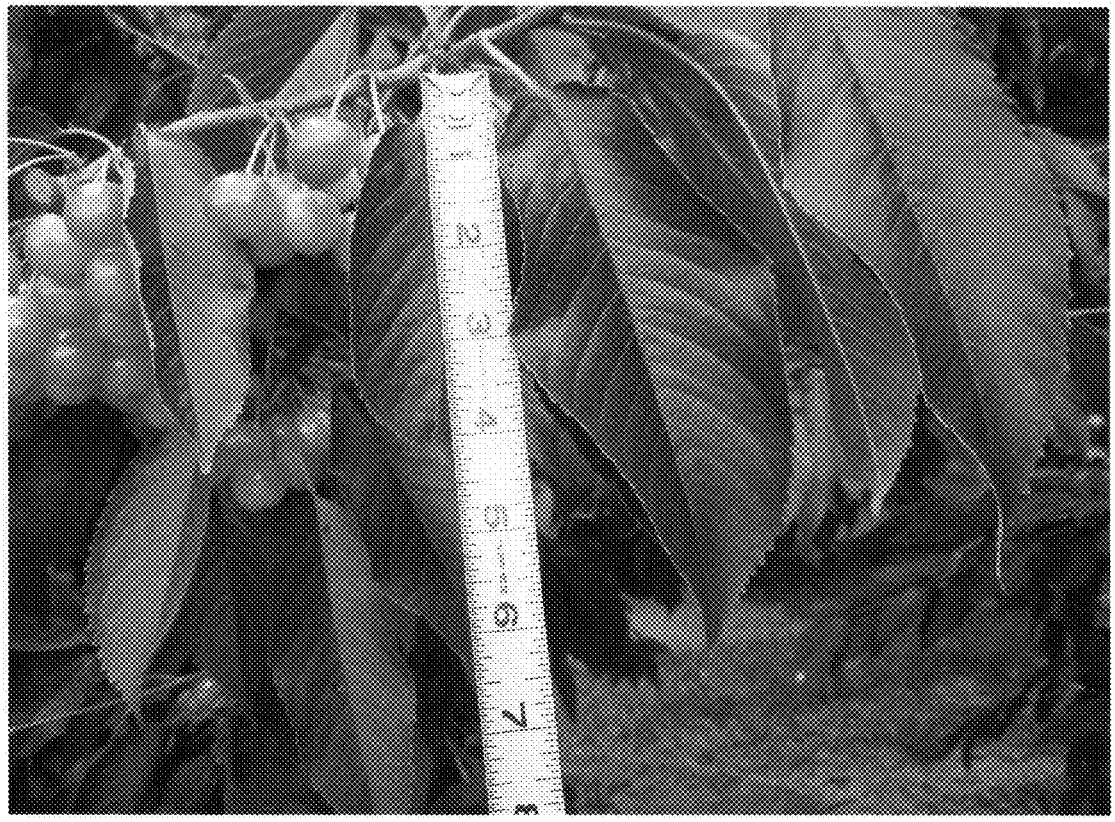
Figure 4:
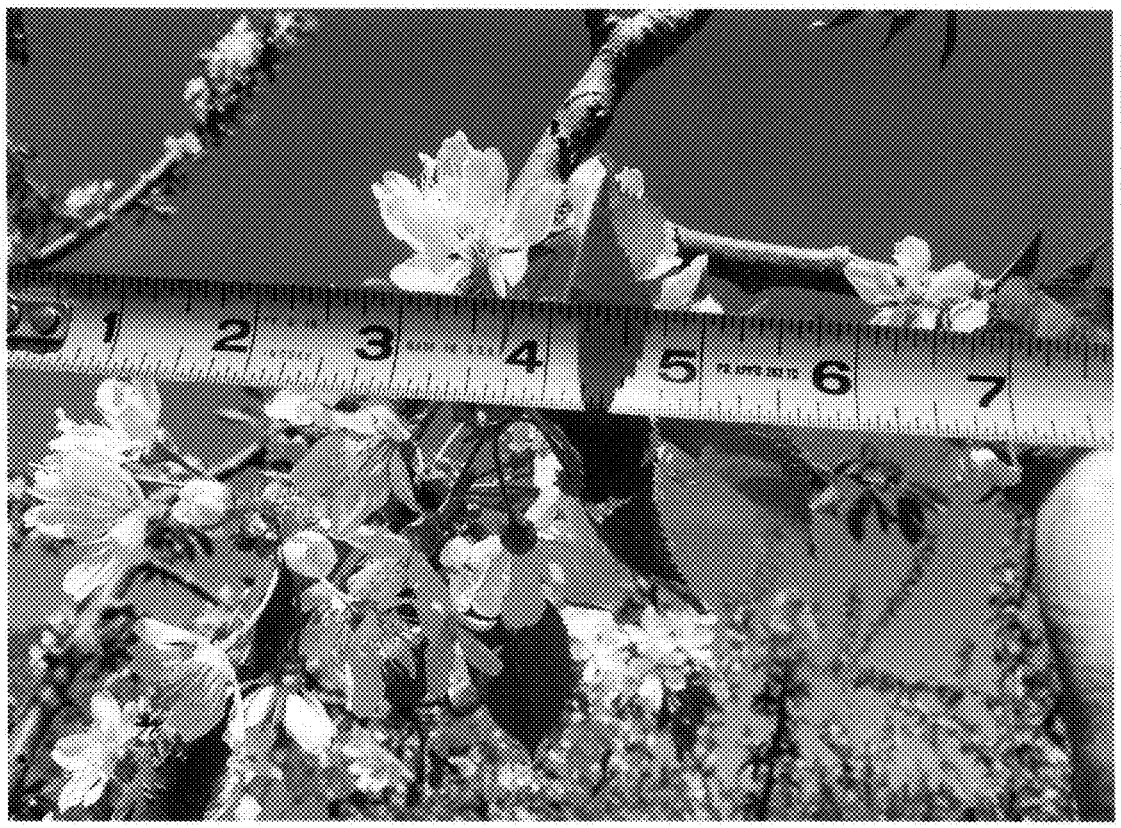
Figure 5:
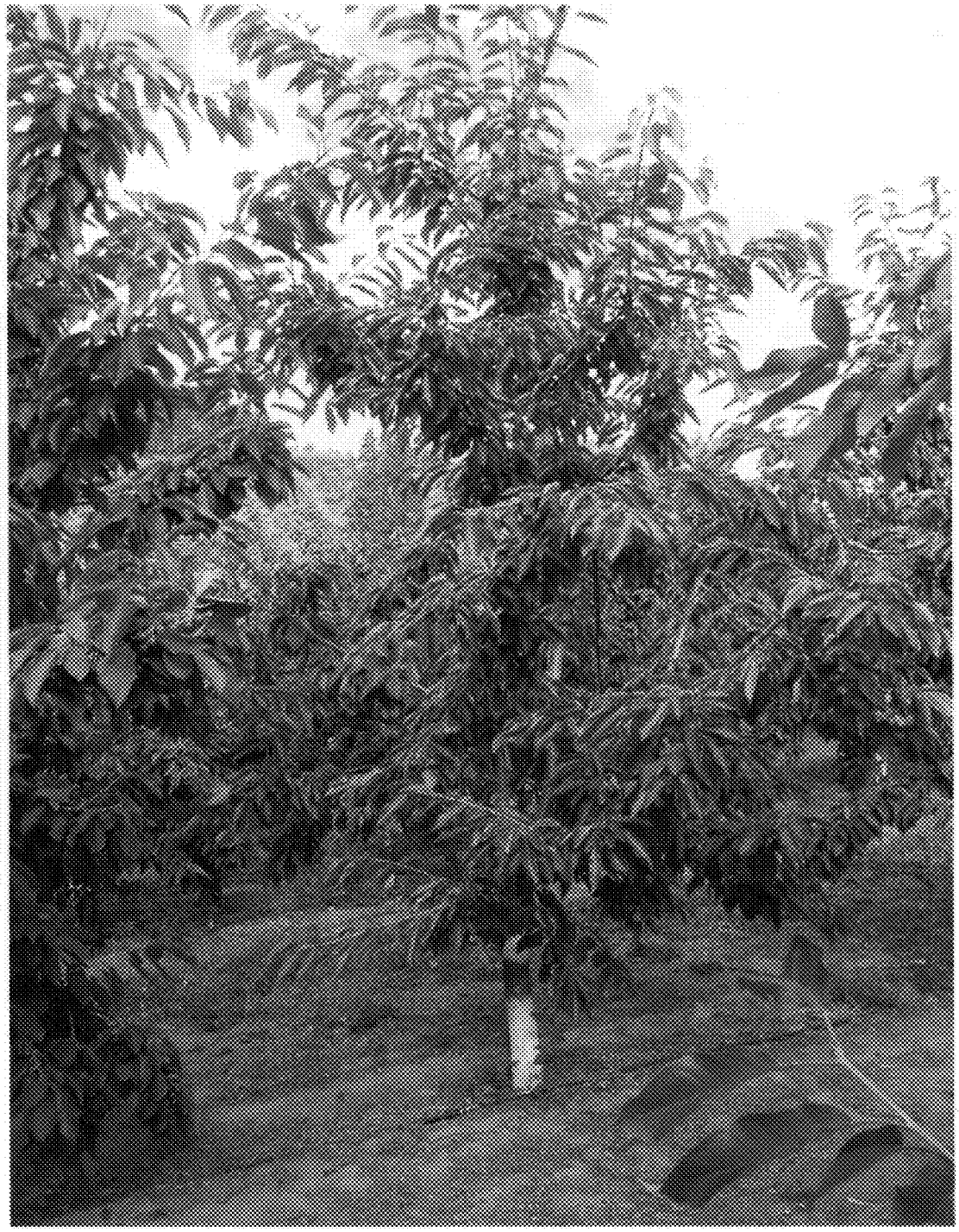

FIG. 1 shows the fruit of the new variety;
FIG. 2 shows sectioned fruit of the variety;
FIG. 3 shows the leaves of the new variety;
FIG. 4 shows the blossoms of the new variety; and
FIG. 5 shows the tree of the new variety.

The colors of this illustration may vary with lighting conditions. Color characteristics of this new variety should therefore be determined with reference to the observations described herein, rather than from these illustrations alone.

DETAILED BOTANICAL DESCRIPTION

The following detailed botanical description is based on observations of the original tree of the variety, planted in 2001 and grown on 'Mazzard' rootstock (not patented). Observations were recorded and photographs taken during the 2007 and 2008 growing seasons at Wenatchee, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The Royal Horticultural Society Colour Chart (2001).

Tree:

*Size.*—Height 3.96 m, spread 2.84 m.
*Branching habit.*—Upright.
*Hardiness.*—Hardy in area tested (USDA Hardiness Zone 6A).
*Productivity.*—6.8 kg per tree (2008 growing season).
*Bearing.*—Annual.
*Trunk.*—Diameter 10.2 cm at 30 cm above soil; Bark smooth, gray 201D; Trunk lenticel width 1 mm to 2 mm, length 8 mm to 19 mm, orange-white 159C.
*Branch.*—First year wood — diameter 0.5 cm at 20 cm from base, length 48.3 cm; Second year wood — diameter 0.8 cm at 20 cm from base, length 73.7 cm; Crotch angle 30° to 50°, texture smooth, greyed-orange 176C, branch lenticel width 2 mm, length varies (about 6 mm), numerous.

Leaves:

*Size.*—Length 15.0 cm, width 5.1 cm.
*Shape.*—Oval, base cuneate, apex acuminate.
*Margin.*—Serrulate.
*Color.*—Upper surface green 137C, lower surface green 135D.
*Midvein.*—Width 2 mm, upper surface yellow-green 137C, lower surface green 142A.
*Petiole.*—Length 32 nun, diameter 3 nun; upper surface red-purple 59C, lower surface green 142A.
*Glands.*—Quantity 1 per leaf; round; length 2 mm, width 2 mm; red-purple 58A.

Flowers:

*Buds.*—Quantity 10 per spur; length 1.7 cm, width 0.6 cm.

*Bloom date.*—First bloom April 27; full bloom date May 8 (2007 growing season, Wenatchee, Wash.).

*Flower color.*—Upper and lower surfaces white N155A.

*Flower diameter.*—3 cm.

*Petals.*—Quantity 5; not touching; margin smooth; length 1.3 cm, width 0.8 cm; shape obcordate, base cuneate, apex obcordate.

*Reproductive organs.*—Stamen — quantity 25 to 30, length 0.5 to 0.8 cm, white, anther yellow 4C, pollen yellow 9A; Pistil — length 1 cm, yellow-green 149C; Stigma — diameter 1 mm, yellow-green 150C; Style — length 8 mm, yellow-green 149C; Ovary — diameter 2 mm, yellow-green 149C; Pedicel — length 2 cm, diameter 1 to 2 mm, green 142C.

Fruit:

*Size.*—Apical diameter 26 mm, axial diameter 30 mm; Average weight 10.3 g.

*Shape.*—Reniform, symmetrical; Pistil end flat to slightly depressed.

*Depth of suture.*—Very shallow.

*Stem.*—Length 40 mm, diameter 2 mm; green 142A.

*Cavity.*—Depth 3 mm, diameter 15 mm.

*Skin.*—Thin, smooth, glossy, tenacious to flesh, no tendency to crack noted; ground color yellow 8C, blush over color red 46B, lenticels inconspicuous.

*Flesh.*—Fine, crisp, firm; yellow 8C.

*Stone.*—Length 11 mm, width 11 mm; round; flesh not tenacious to stone; greyed-orange 161B.

*Maturity date.*—July 20 (2007 growing season, Wenatchee, Wash.), about 11 days earlier than 'Rainier'.

*Fruit analysis.*—23% to 27% Brix at maturity; Acidity 0.679; Penetrometer 385.40.

*Market use.*—Fresh market.

Disease/pest resistance/susceptibility: None observed.

The invention claimed is:

1. What is claimed is a new and distinct cherry tree as shown and described herein.

* * * * *